United States Patent
Kim et al.

(10) Patent No.: US 11,519,918 B2
(45) Date of Patent: Dec. 6, 2022

(54) METHOD FOR QUANTIFICATION OF AMINO ACIDS USING CELL-FREE PROTEIN SYNTHESIS SYSTEM

(71) Applicant: The Industry & Academic Cooperation in Chungnam National University (IAC), Daejeon (KR)

(72) Inventors: Dong-Myung Kim, Daejeon (KR); Tae Hyeon Yoo, Gyeonggi-do (KR); Kyung-Ho Lee, Daejeon (KR); Yeon-Jae Jang, Daejeon (KR)

(73) Assignee: THE INDUSTRY & ACADEMIC COOPERATION IN CHUNGNAM NATIONAL UNIVERSITY (IAC), Daejeon (KR)

( * ) Notice: Subject to any disclaimer, the term of this patent is extended or adjusted under 35 U.S.C. 154(b) by 502 days.

(21) Appl. No.: 16/633,805

(22) PCT Filed: Jul. 24, 2018

(86) PCT No.: PCT/KR2018/008343
§ 371 (c)(1),
(2) Date: Jan. 24, 2020

(87) PCT Pub. No.: WO2019/022467
PCT Pub. Date: Jan. 31, 2019

(65) Prior Publication Data
US 2021/0123929 A1    Apr. 29, 2021

(30) Foreign Application Priority Data
Jul. 24, 2017 (KR) .................... 10-2017-0093657

(51) Int. Cl.
G01N 33/68    (2006.01)
C12Q 1/52     (2006.01)

(52) U.S. Cl.
CPC ........... *G01N 33/6893* (2013.01); *C12Q 1/52* (2013.01); *G01N 2333/91188* (2013.01)

(58) Field of Classification Search
None
See application file for complete search history.

(56) References Cited

FOREIGN PATENT DOCUMENTS

| | | |
|---|---|---|
| JP | 07-184693 | 7/1995 |
| JP | 2577878 | 11/1996 |
| KR | 10-0733712 | 6/2007 |
| KR | 10-0966655 | 6/2010 |
| KR | 10-1671688 | 11/2016 |
| KR | 10-2017-0014459 | 3/2018 |

OTHER PUBLICATIONS

Blau, Nenad, Francjan J. van Spronsen, and Harvey L. Levy. "Phenylketonuria." *The Lancet* 376.9750 (2010): 1417-1427.
Chace, D. H., et al. "Rapid diagnosis of homocystinuria and other hypermethioninemias from newborns' blood spots by tandem mass spectrometry." *Clinical chemistry* 42.3 (1996): 349-355.
Chace, Donald H., et al. "Rapid diagnosis of maple syrup urine disease in blood spots from newborns by tandem mass spectrometry." *Clinical Chemistry* 41.1 (1995): 62-68.
Gu, Yu, et al. "Perioperative dynamics and significance of amino acid profiles in patients with cancer." *Journal of translational medicine* 13.1 (2015): 35.
Harris, H., et al. "The pattern of amino-acid excretion in cystinuria." *Annals of human genetics* 19.3 (1955): 196-208.
Hopwood, Jennifer, et al. "A fast and sensitive assay for measuring the activity and enantioselectivity of transaminases." *Chemical Communications* 47.2 (2010): 773-775.
Iyer, R., et al. "The human arginases and arginase deficiency." *Journal of inherited metabolic disease* 21 (1998): 86-100.
Kim, Dong Myung, "Genome-scale Expression and in Situ Analysis of Proteins though the Combination of Cell-fee Protein Synthesis and Bio-sensing Technologies", Ministry of Science and Technology Mid-career Researcher Program(Key Research) Final Report, Aug. 2010, pp. 1-49. Cited in International Search Report of PCT/KR2018/008343.
Lai, Hong-Shiee, et al. "Plasma free amino acid profile in cancer patients." *Seminars in cancer biology*. vol. 15. No. 4. Academic Press, 2005.

(Continued)

*Primary Examiner* — Robert J Yamasaki
(74) *Attorney, Agent, or Firm* — ParkerHighlander, PLLC

(57) ABSTRACT

The present invention relates to a method for quantification of amino acids using a cell-free protein synthesis system. Specifically, the present invention relates to a method for quantification of amino acids, comprising: (a) preparing a reaction mixture for cell-free protein synthesis without target amino acids; (b) performing cell-free protein synthesis by mixing an assay sample containing target amino acids with the reaction mixture for cell-free protein synthesis; (c) measuring the signal intensity of the synthesized protein; and (d) calculating the concentration of the target amino acids by comparing the measured signal intensity with the standard concentration curve for each amino acid according to the protein signal produced using a standard sample, a method for providing information for diagnosing an amino acid metabolism-related disease using the same, a method for screening a material for prevention or treatment of an amino acid metabolism-related disease, and a method for screening a transaminase substrate. The method for quantification of amino acids according to the present invention can quantify amino acids in a short time at a low cost, and thus can be useful in various industries.

19 Claims, 10 Drawing Sheets

(56) References Cited

OTHER PUBLICATIONS

Mathew, Sam, et al. "High throughput screening methods for ω-transaminases," *Biotechnology and bioprocess engineering* 18.1 (2013): 1-7.
Miyagi, Yohei, et al. "Plasma free amino acid profiling of five types of cancer patients and its application for early detection." *PloS one* 6.9 (2011).
Mudd, S. Harvey, et al. "Homocystinuria: an enzymatic defect." *Science* (1964): 1443-1445.
Park, Ji Young, "High-throughput Screening of Glycosyltransferase in a Cell-free Protein Synthesis System", Chungnam National University, Graduate School, Master's thesis, 2012. pp. 1-61. Cited in International Search Report of PCT/KR2018/008343.
Prensky, Arthur L., and Hugo W. Moser. "Brain lipids, proteolipids, and free amino acids in maple syrup urine disease." *Journal of neurochemistry* 13.9 (1966): 863-874.
Saudubray, Jean-Marie, and Daniel Rabier. "Biomarkers identified in inborn errors for lysine, arginine, and ornithine." *The Journal of nutrition* 137.6 (2007): 1669S-1672S.
Stephenson, J. B. P., and M. S. McBean. "Diagnosis of phenylketonuria (phenylalanine hydroxylase deficiency, temporary and permanent)." *British medical journal* 3.5565 (1967): 579.

[FIG. 1]
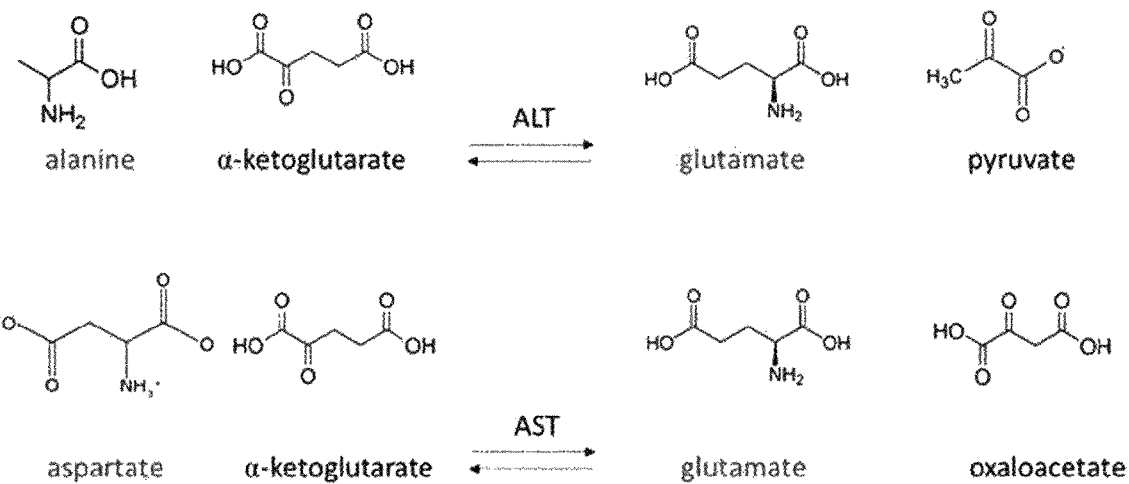
[FIG. 2]
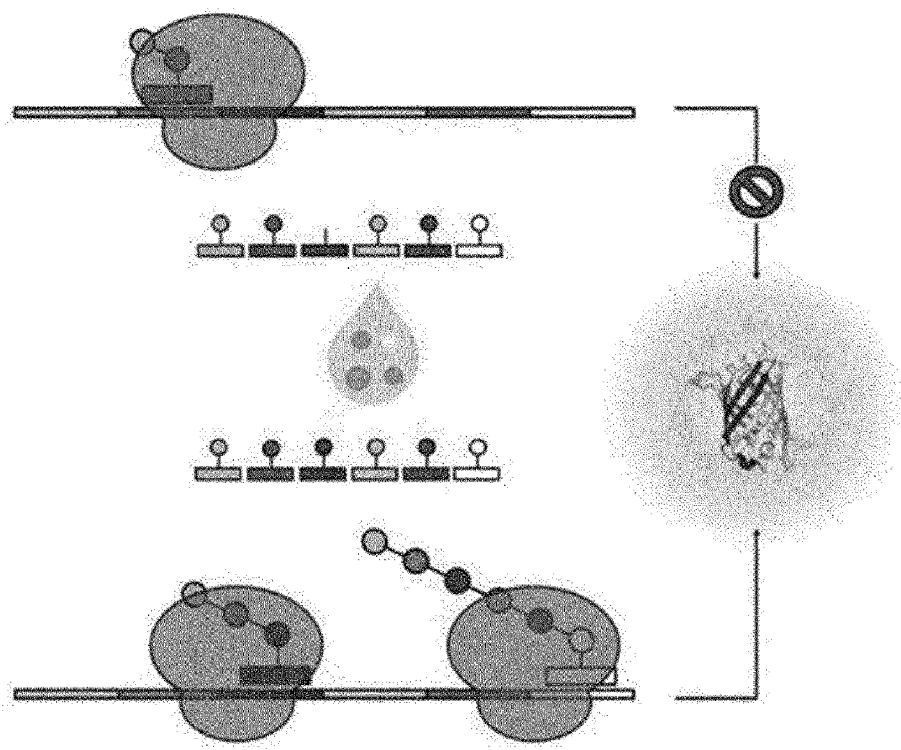

[FIG. 3]
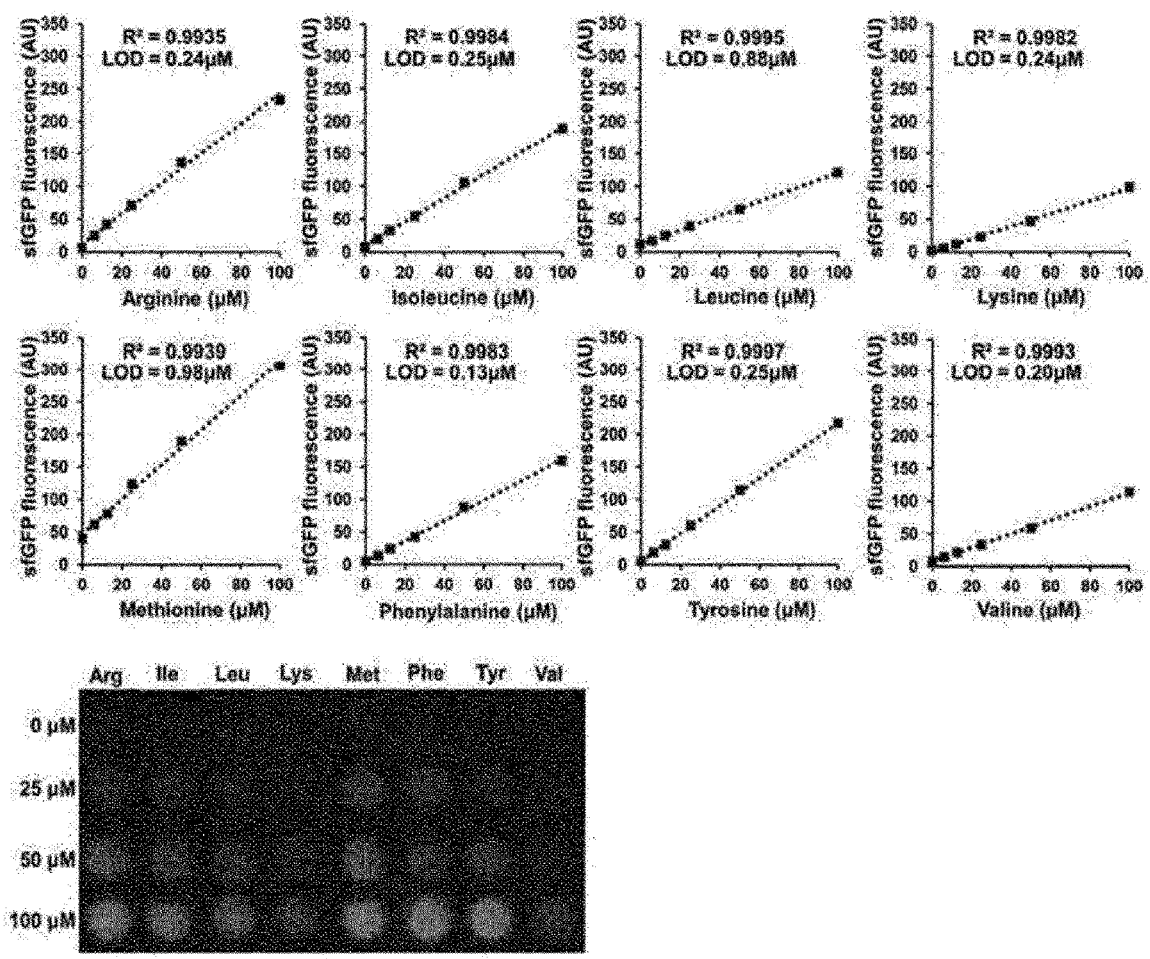

[FIGS. 4A-4B]
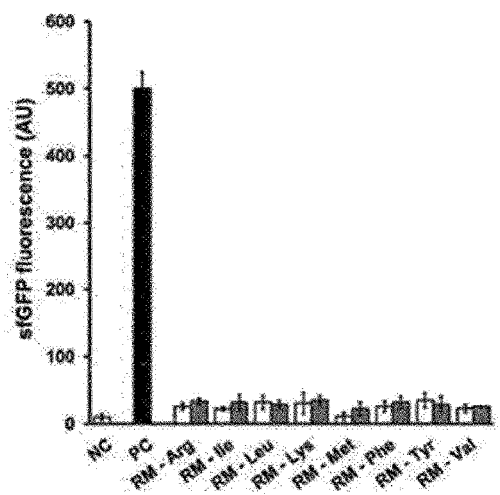
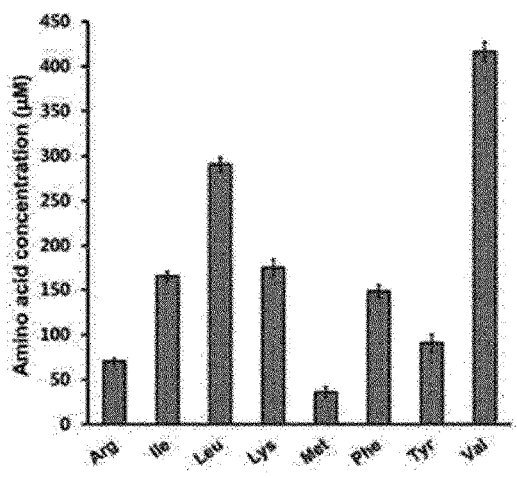
[FIGS. 5A-5C]
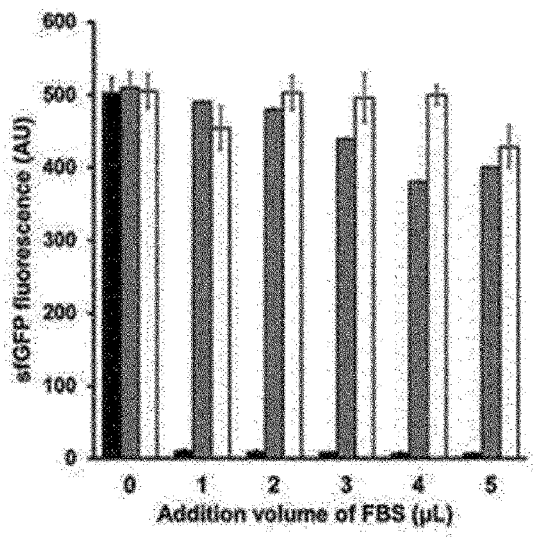
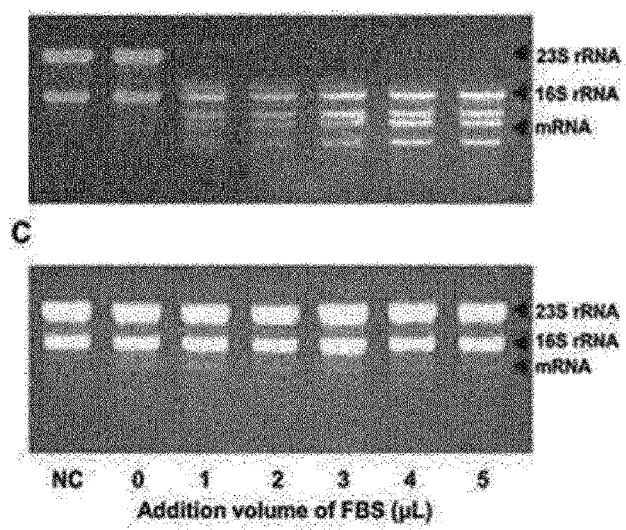

[FIG. 6]
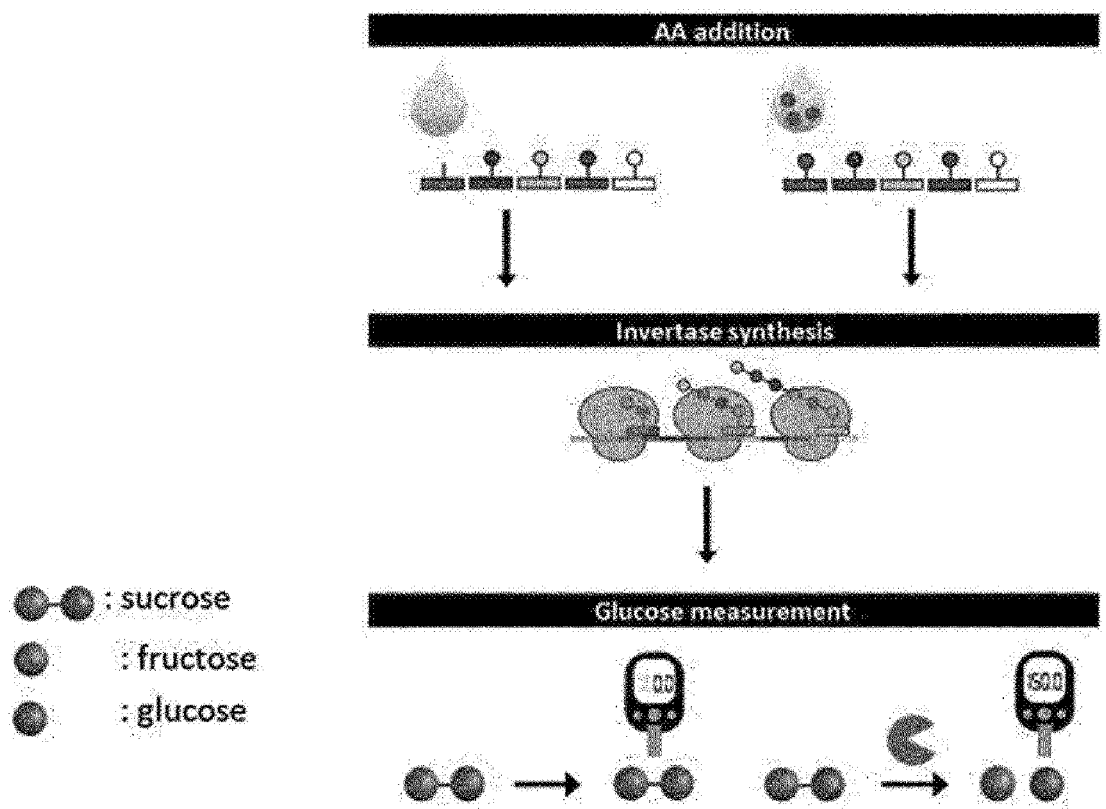

[FIGS. 7A-7B]
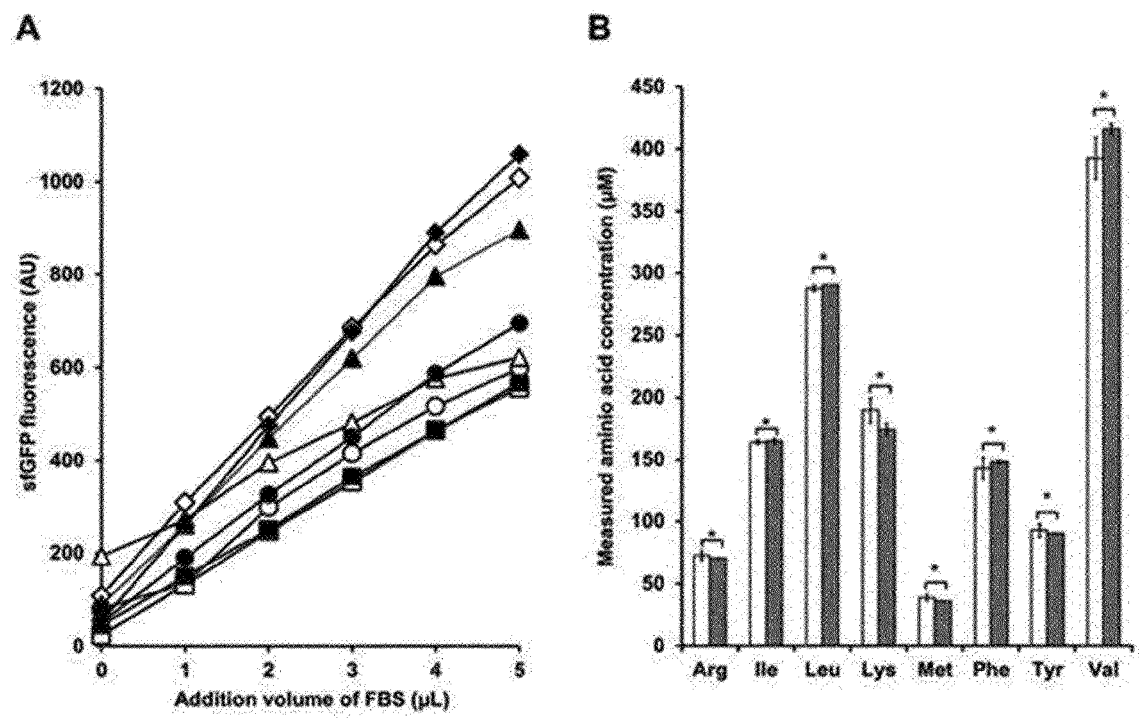

[FIG. 8]
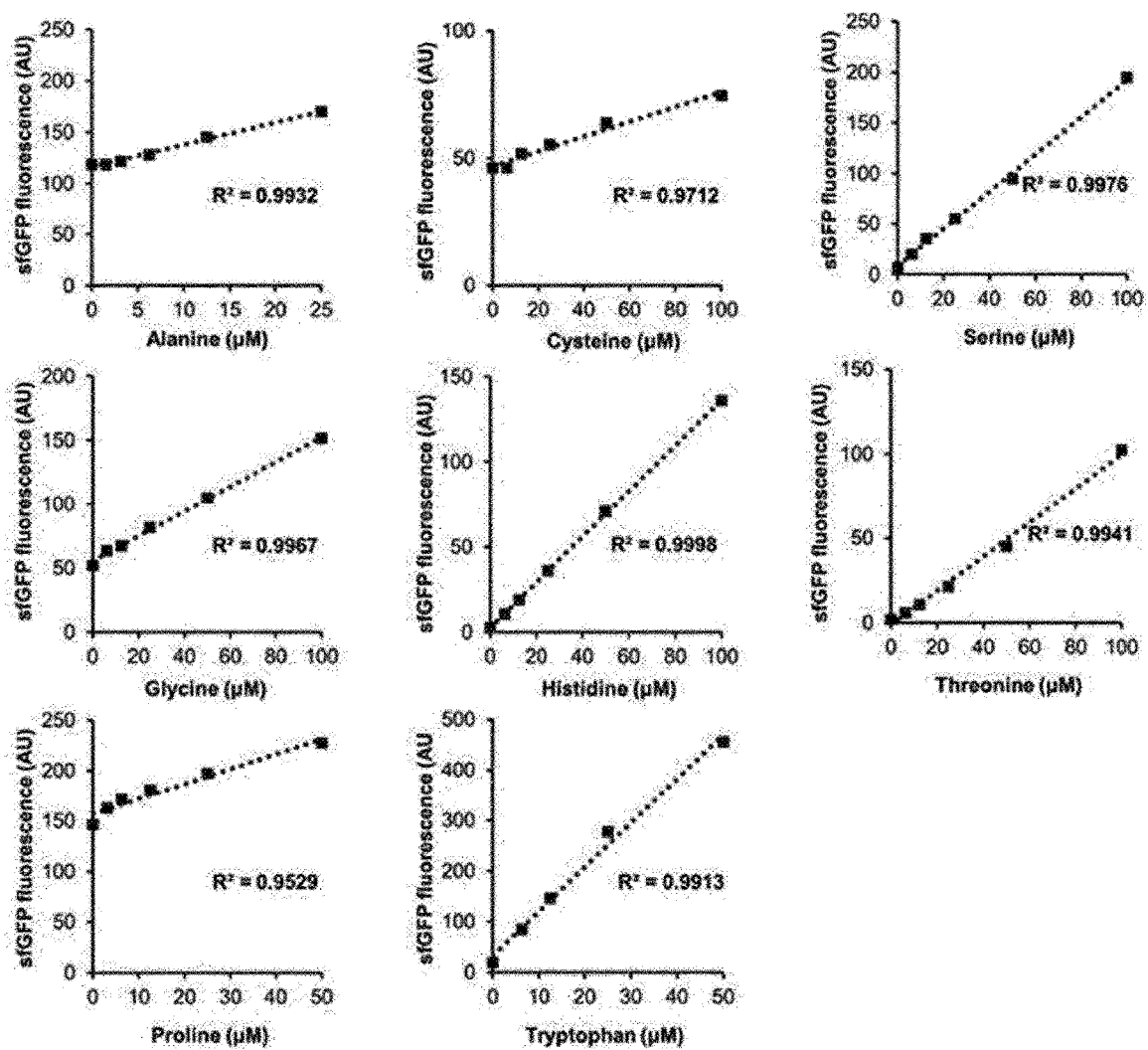

[FIG 9]
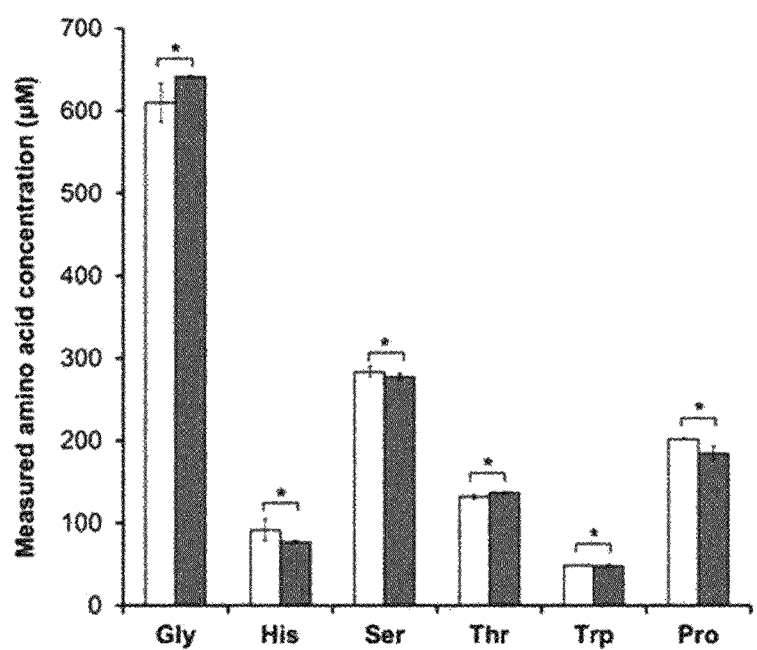

[FIG. 10]
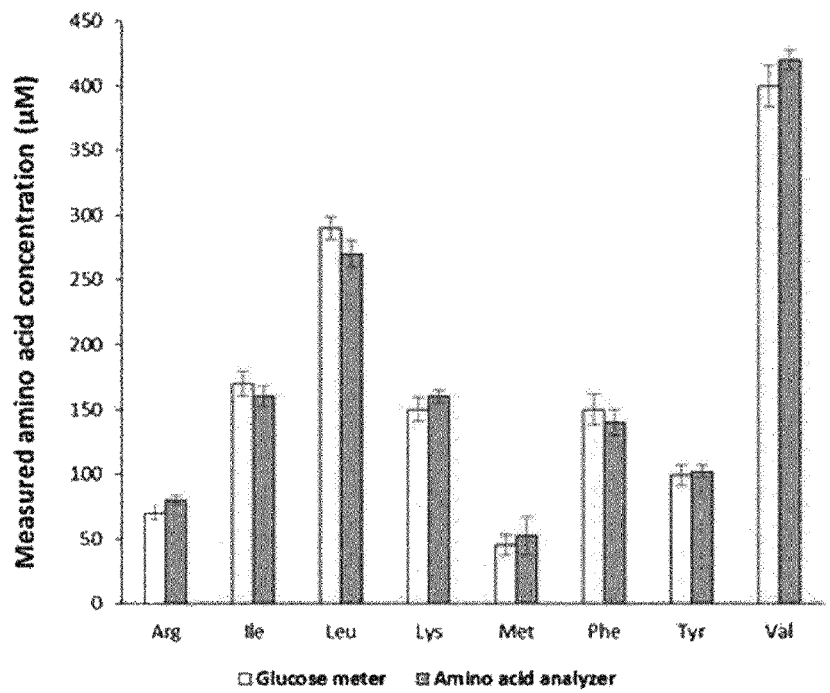

[FIG. 11]
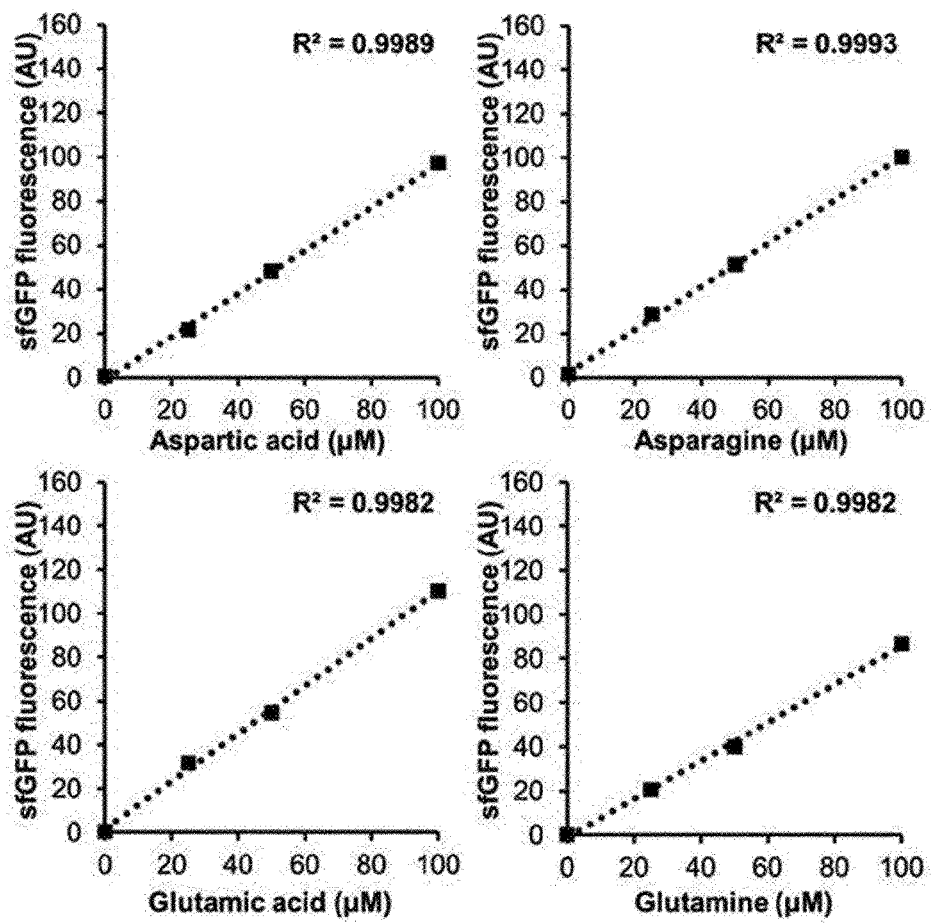

[FIG. 12]
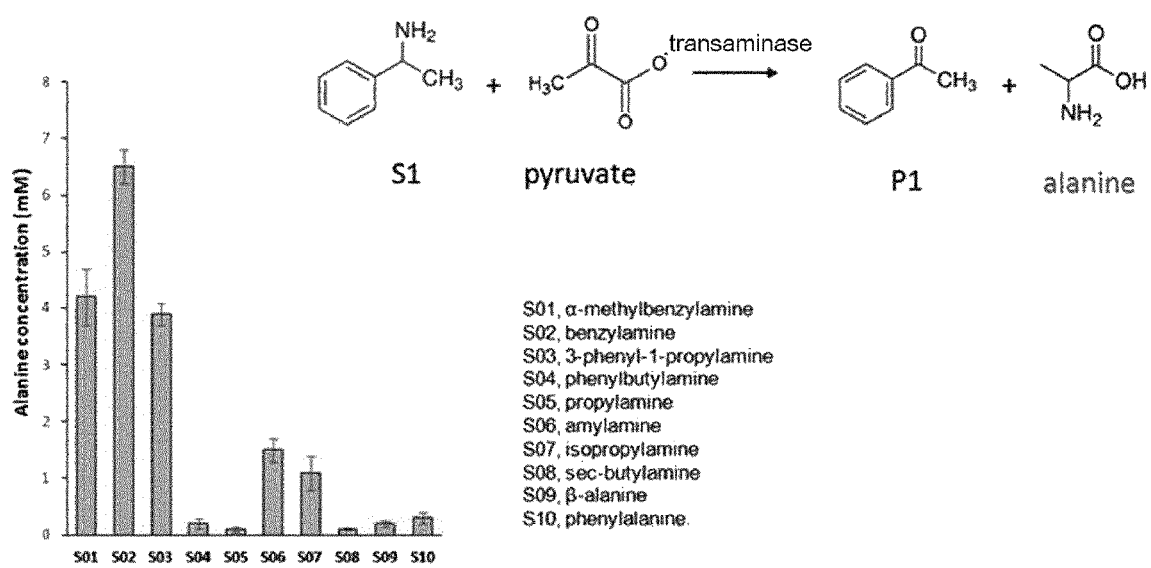

METHOD FOR QUANTIFICATION OF AMINO ACIDS USING CELL-FREE PROTEIN SYNTHESIS SYSTEM

This application is a national phase application under 35 U.S.C. § 371 of International Application No. PCT/KR2018/008343, filed Jul. 24, 2018, which claims priority to Korean Application No. 10-2017-0093657, filed Jul. 24, 2017. The entire text of each of the above referenced disclosures is specifically incorporated herein by reference.

TECHNICAL FIELD

The present invention relates to a method for quantification of amino acids using a cell-free protein synthesis system. Specifically, the present invention relates to a method for quantification of amino acids, including: (a) preparing a reaction mixture for cell-free protein synthesis without target amino acids; (b) performing cell-free protein synthesis by mixing an assay sample containing target amino acids with the reaction mixture for cell-free protein synthesis; (c) measuring the signal intensity of the synthesized protein; and (d) calculating the concentration of the target amino acids by comparing the measured signal intensity with the standard concentration curve for each amino acid according to the protein signal produced using a standard sample, a method for providing information for diagnosing an amino acid metabolism-related disease using the same, a method for screening a material for prevention or treatment of an amino acid metabolism-related disease, and a method for screening a transaminase substrate.

BACKGROUND ART

Amino acid analysis is actively applied in a diverse range of areas including food, environment, fine chemistry, pharmaceutical, diagnostics, etc. As a representative example, the food industry utilizes quantification of amino acids when analyzing the content of nutrients such as amino acids contained in food, and additionally, quantification of amino acids is employed in the manufacture of animal feeds, as the content and composition of various amino acids are considered essential for the animal feeds. In the fine chemical industry, a transfer reaction of amine groups by enzymes such as transaminase, a decomposition reaction of carboxyl groups by amino acid decarboxylase, etc. are used for the synthesis of various pharmaceutical intermediates, etc. In many cases, these reactions involve the production and conversion of amino acids, and thus, the amino acid analysis technique can be effectively used as a screening tool for screening substrates, and discovering and engineering new enzymes in reactions catalyzed by these enzymes.

Additionally, quantification of amino acids is also actively applied in the fields of pharmaceuticals and diagnostics. As an example, since plasma free amino acids are redistributed or translocated to support the growth and development of cancer, it has been known that the profile of plasma free amino acids in cancer patients exhibiting a distinctive morphology from those of normal people can be used as a new biomarker for diagnosis or prognosis in cancer patients (Yu Gu, Gu et al. *Journal of Translational Medicine* (2015) 13:35; Hong-Shiee Lai, *Seminars in Cancer Biology* 15 (2005) 267-276; Miyagi Y, *PLoS One.* 2011; 6(9):e24143).

Further, as amino acid metabolic disorders such as arginase deficiency, cystinuria, maple syrup urine disease, hyperlysinemia, homocystinuria, hypermethioninemia, and phenylketonuria interfere with normal amino acid metabolism (Layer R., *Inherited Metab. Dis.* 2016, 21, 86-100.; Harris H., *Ann. Hum. Genet.* 1995, 19, 196-208.; Chace D. H., *Clin. Chem.* 1995, 41, 32-38.; Prensky A. L., *Neurochem.* 1966, 13, 863-874.; Saudubray J. M., *Nutr.* 2007, 137, 1669S-1672S.; Chace D. H., *Clin. Chem.* 1996, 42, 349-355.; Mudd S. H., *Science* 1964, 143, 1443-1445.; Blau N., *Lancet* 2010, 376, 1417-1427.; Stephenson J. B. P., *Br. Med. J.* 1967, 3, 579-581.), such amino acid metabolic disorders can be easily diagnosed when the relevant amino acids found in the body are quantified. Such amino acid analysis technique can be used for the diagnosis of various diseases in addition to the diagnosis of the amino acid metabolic diseases described above. For example, an alanine aminotransferase (ALT)/aspartate aminotransferase (AST) activity assay, which is a method commonly used for diagnosing liver diseases, is carried out according to the activity for the reactions catalyzed by ALT and AST in blood samples. Thus, methods of measuring the concentrations of alanine, aspartate, and glutamate involved in these reactions can be used in the liver function test.

Current methods for quantification of amino acids are based on liquid chromatography separation with or without their derivatization, which involve complicated procedures, a long processing time, and thus require improvements due to costly laboratory setup. As an alternative approach, a method of analyzing amino acids by a biological method has recently been reported, including a method using auxotrophic *Escherichia coli* strains, etc. However, the method has limitations in that it would be difficult to establish a strain suitable for target amino acids to be analyzed, and maintenance of cell viability remains a challenging issue.

Meanwhile, cell-free protein synthesis has emerged as a powerful approach that can overcome many of the limitations associated with cell-based protein synthesis. Unlike methods using living cells in which protein synthesis takes place within the highly complex and ordered cellular structure, cell-free synthesis takes place in vitro in an open system, and thus, the constituents of cell-free synthesis can be individually manipulated without limitation. Additionally, there is an advantage in that the operation is simple due to utilization of a simple equipment. Accordingly, a method for cell-free protein synthesis using a yeast extract as an amino acid source, a method for cell-free protein synthesis involved with pH control using an enzyme, etc. have been developed (Korean Patent Laid-Open Publication No. 10-2017-0014459, Korean Patent No. 10-1671688).

DISCLOSURE

Technical Problem

Under these circumstances, the present inventors have made extensive efforts to develop a method for simply quantifying amino acids, and as a result, the present invention has been implemented based on the finding that amino acids present in an assay sample can be quantitatively analyzed when the characteristic of a cell-free protein synthesis system that the progress of protein synthesis depends on the exogenous addition of amino acids is used, and has been completed by confirming that target amino acids can be quantified rapidly at a low cost through the development of a method of directly or indirectly measuring the signal intensity of a reporter protein produced by the cell-free protein synthesis.

Technical Solution

It is one object of the present invention to provide a method for quantification of amino acids, including:

(a) preparing a reaction mixture for cell-free protein synthesis without target amino acids;

(b) performing cell-free protein synthesis by mixing an assay sample containing target amino acids with the reaction mixture for cell-free protein synthesis;

(c) measuring the signal intensity of the synthesized protein; and (d) calculating the concentration of the target amino acids by comparing the measured signal intensity with the standard concentration curve for each amino acid according to the protein signal produced using a standard sample.

It is another object of the present invention to provide a method of providing information for diagnosing an amino acid metabolism-related disease, including comparing the concentration of amino acids quantified according to the above method.

It is still another object of the present invention to provide a method for screening a material for prevention or treatment of an amino acid metabolism-related disease, including:

(a) treating a candidate material for prevention or treatment of an amino acid metabolism-related disease with an assay sample isolated from a living organism;

(b) measuring the concentration of target amino acids contained in the assay sample treated with the candidate material according to the above method; and (c) comparing the amino acid concentration of step (b) with a normal control group.

It is still another object of the present invention to provide a method for screening a transaminase substrate, including:

(a) reacting a transaminase with a mixture of a candidate amine donor substrate and amine acceptor substrate;

(b) measuring the concentration of amino acids contained in the reaction solution after completion of the reaction; and (c) comparing the amino acid concentration of step (b) with a control group It is still another object of the present invention is to provide a method for screening a transaminase, including:

(a) reacting a candidate enzyme with a mixture of an amine donor substrate and amine acceptor substrate;

(b) measuring the concentration of amino acids contained in the reaction solution after completion of the reaction; and (c) comparing the amino acid concentration of step (b) with a control group.

Advantageous Effects

The method for quantification of amino acids according to the present invention can quantify amino acids in a short time at a low cost, and thus can be useful in various industries.

BRIEF DESCRIPTION OF DRAWINGS

FIG. 1 is a reaction scheme showing the reaction catalyzed by ALT and AST, which are used as major markers of liver function diagnosis.

FIG. 2 is a schematic diagram showing the concept of a cell-free protein synthesis system used in the method for quantification of amino acids of the present invention.

FIG. 3 shows the standard concentration curves illustrating the concentrations of arginine, isoleucine, leucine, lysine, methionine, phenylalanine, tyrosine, and valine for fluorescence intensity of super-folder green fluorescent protein (sfGFP) and a fluorescence image of sfGFP.

FIGS. 4A-4B show the results obtained when FBS is used as an assay sample. Specifically, A is a graph showing the sfGFP fluorescence signals when unheat-treated FBS was used, where NC shows the result obtained from a negative control reaction mixture without sfGFP DNA, PC shows the result obtained from the reaction with a positive control reaction mixture containing sfGFP DNA and all amino acids, and RM-Arg, RM-Ile, RM-Leu, RM-Lys, RM-Met, RM-Phe, RM-Tyr, or RM-Val shows the results obtained from the reaction with incomplete reaction mixtures devoid of arginine, isoleucine, leucine, lysine, methionine, phenylalanine, tyrosine or valine, respectively. B is a graph showing the concentration of amino acids contained in the unheat-treated FBS analyzed by a standard amino acid analyzer, where Arg, Ile, Leu, Lys, Met, Phe, Tyr, or Val represents arginine, isoleucine, leucine, lysine, methionine, phenylalanine, tyrosine or valine, respectively.

FIGS. 5A-5C show the results obtained when unheat-treated FBS, heat-treated FBS, or heat-treated and filtered FBS was used as an assay sample. Specifically, A is a graph showing the sfGFP fluorescence signals when unheat-treated FBS (black bar), heat-treated FBS (grey bar), and heat-treated and filtered FBS (white bar) were used. B is an image showing RNA present in the reaction mixtures when unheat treated FBS was used. C is an image showing RNA present in the reaction mixtures when heat-treated and filtered FBS was used.

FIG. 6 is a schematic diagram showing an overview of quantification of amino acids using a glucose meter.

FIGS. 7A-7B show the results obtained when heat treated and filtered FBS was used as an assay sample. A is a graph showing the sfGFP fluorescence signals when incomplete reaction mixtures devoid of arginine (white circle), isoleucine (white rhombus), leucine (black rhombus), lysine (white square), methionine (white triangle), phenylalanine (black circle), tyrosine (black square) or valine (black rhombus) were used. B is a graph showing the concentration of amino acids quantified according to the present invention (white bars) and the concentration of amino acids analyzed by a standard amino acid analyzer (grey bars). * represents $p>0.05$.

FIG. 8 shows standard curve graphs illustrating the concentrations of alanine, cysteine, glycine, histidine, proline, serine, threonine, or tryptophan for sfGFP fluorescence intensity.

FIG. 9 is a graph showing the results obtained when heat-treated and filtered FBS was used as an assay sample, illustrating the concentration of glycine, histidine, serine, threonine, tryptophan, or proline contained in the FBS. * represents $p>0.05$.

FIG. 10 is a graph showing the concentration of amino acids quantified using a glucose meter (white bars) compared to the analysis results obtained using a standard amino acid analyzer (gray bars).

FIG. 11 shows the results obtained when recombinant protein mixtures were used as cell-free protein reaction mixtures, and shows standard curve graphs illustrating the concentration of aspartic acid, asparagine, glutamic acid, or glutamine for sfGFP fluorescence intensity.

FIG. 12 shows a diagram schematically illustrating the process of amino acid production by a transamination reaction and a graph showing the results of screening the transaminase substrate through the cell-free protein synthesis.

DETAILED DESCRIPTION OF PREFERRED EMBODIMENTS

In order to achieve the objects above, one aspect of the present invention provides a method for quantification of amino acids, including:

(a) preparing a reaction mixture for cell-free protein synthesis without target amino acids;

(b) performing cell-free protein synthesis by mixing an assay sample containing target amino acids with the reaction mixture for cell-free protein synthesis;

(c) measuring the signal intensity of the synthesized protein; and (d) calculating the concentration of the target amino acids by comparing the measured signal intensity with the standard concentration curve for each amino acid according to the protein signal produced using a standard sample.

In the present invention, there is provided a simple and economical method for quantification of amino acids based on the polymerization of amino acids into a signal-generating protein, i.e. a reporter protein.

In general, the cell-free protein synthesis is dependent on the exogenous addition of missing components. In other words, when a reaction mixture for cell-free protein synthesis devoid of specific constituents necessary for protein synthesis is complemented with the missing components, the protein synthesis is carried out. Based on this principle, the present inventors developed a method for quantification of amino acids by selectively omitting specific components from the cell-free protein reaction mixture.

Specifically, the method of the present invention harnesses a cell-free protein synthesis system that generates specific signals in response to exogenous amino acids. More specifically, the method is based on the principle that when an assay sample containing the target amino acid to be quantified is mixed with a cell-free synthetic reaction mixture without the target amino acid and incubated, a reporter protein is rapidly synthesized, and a signal of the synthesized protein or a signal generated by the reaction catalyzed by the synthesized protein is linearly proportional to the concentration of the amino acids.

Currently methods for quantification of amino acids require chemical derivatization of amino acids and expensive chromatography equipment. In contrast, the method of the present invention enables the quantification of amino acids at a lower cost by allowing a direct conversion of amino acid titers into bio signals in a short time. In particular, the method according to the present invention can detect amino acids at concentrations as low as 100 nM, and can quantify amino acids associated with diseases contained in biological samples. Therefore, the present invention can be widely applied for various purposes such as immediate analysis of amino acids, on-site diagnosis of diseases, etc.

In the present invention, the step (a) is a step for preparing a reaction mixture for cell-free protein synthesis without target amino acids.

As used herein, the term "target amino acid" refers to an amino acid to be quantified by the method according to the present invention. Specifically, the target amino acid may be at least one selected from the group consisting of arginine, isoleucine, leucine, lysine, methionine, phenylalanine, tyrosine, valine, alanine, cysteine, serine, glycine, histidine, threonine, proline, tryptophan, aspartic acid, asparagine, glutamic acid, and glutamine, and more specifically, it may be at least one selected from the group consisting of arginine, isoleucine, leucine, lysine, methionine, phenylalanine, tyrosine, valine, alanine, cysteine, serine, glycine, histidine, threonine, proline, and tryptophan, but is not limited thereto.

As used herein, the term "cell-free protein synthesis" refers to carrying out protein synthesis in vitro, such as in test tubes, etc., which usually takes place within cells, and is the production of a target protein in a short time by extracting only the components essential for protein production, i.e., intracellular protein synthesis apparatus and their factors from the cell and artificially repeating only the synthesis process of the protein in a state in which the physiological control mechanism of the cell is excluded from the outside of the cell. In particular, the protein biosynthesis apparatus required for cell-free protein synthesis, i.e., ribosomes, initiation factors, elongation factors, termination factors, aminoacyl tRNA synthetase, RNA polymerase, etc., contained in a cell extract may be used, or may be added separately or produced separately by genetic recombination techniques to be used.

As used herein, the term "reaction mixture for cell-free protein synthesis" refers to a material containing components for carrying out the cell-free protein synthesis. Specifically, a cell extract or a mixture of recombinant proteins including a protein biosynthesis apparatus such as ribosomes, initiation factors, elongation factors, termination factors, release factors, aminoacyl tRNA synthetase, etc. necessary for protein production may be included, but is not limited.

Specifically, the cell extract may be an extract of *E. coli*, wheat germs, rabbit reticulocytes, yeasts, Chinese Hamster ovary cells, or HeLa cells, and more specifically, it may be an *E. coli* extract, but is no limited thereto as long as it can be used in the cell-free protein synthesis reaction.

Additionally, the recombinant protein may be prepared from the components necessary for protein production by recombinant techniques, and may specifically be an initiation factor such as IF1, IF2 and IF3, an elongation factor such as EF-G, EF-Tu and EFTs, a release factor such as RF1, RF2 and RF3, a termination factor such as RRF, aminoacyl-tRNA synthetases, methionyl-tRNA transformylase, RNA polymerase and ribosome. The mixture of recombinant proteins may include all of the components necessary for cell-free protein synthesis, and may specifically include at least one selected from the group consisting of an initiator factor, elongation factor, release factor, termination factor, aminoacyl-tRNA synthetase, methionyl-tRNA transformylase, RNA polymerase and ribosome. When the recombinant protein or a mixture thereof is used, it is possible to exclude enzymes that use the target amino acid as a substrate, and thus all kinds of amino acids can be quantified.

For the purposes of the present invention, the reaction mixture for cell-free protein synthesis may not include the target amino acids.

Additionally, for the purpose of the present invention, the mixture may include a polynucleotide encoding a reporter protein.

As used herein, the term "reporter protein" is a labelled protein that generates a signal that can easily identify the production or synthesis thereof, in particular, the signal may be in various forms such as luminescence, fluorescence, phosphorescence, color development, electron transfer, etc.

Specifically, the reporter protein may be a super-folder green fluorescent protein (sfGFP), green fluorescent protein (GFP), yellow fluorescent protein (YFP), red fluorescent protein (RFP), mCherry fluorescent protein, lactamase, galactosidase, horseradish peroxidase (HRP), or glucose oxidase, but is not limited thereto. The fluorescent proteins among the above proteins measure the fluorescence of the fluorescent proteins accumulated in the cell-free synthetic reaction solution, or in the case of the enzymes, the activity is directly carried out using a substrate corresponding to each enzyme. As another possible measurement method, a glucose meter, which is widely used world-wide as a personal diagnostic equipment, including Korea, may be used. In this case, enzymes, such as invertase, maltase, glucoamylase, etc., that dissociate glucose from disaccharides and polysaccharides containing glucose such as sucrose, maltose, starch, etc. may be used instead of the fluorescent proteins and polynucleotides of the enzymes as a template of the cell-free protein synthesis reaction. When these enzymes are produced in the cell-free synthesis system, the produced enzymes are used to catalyze the reaction by which glucose is generated from sucrose, maltose, starch, etc., and then the produced glucose is quantified using a glucose meter to determine the concentration of amino acids in the sample using the proportional correlation of the concentration of amino acid-synthesized enzyme-glucose.

As used herein, the term "polynucleotide encoding a reporter protein" refers to a reporter gene, and may specifically be DNA (deoxyribonucleic acid) of the gene. In particular, the nucleotide sequence of the gene may be obtained from a known database such as GenBank of NCBI, etc.

In a specific embodiment of the present invention, reaction mixtures for cell-free protein synthesis containing components necessary for the cell-free protein synthesis such as *E. coli* strain BL21-Star (DE3) cell extracts, plasmids containing polynucleotides encoding sfGFP, and ribonucleoside triphosphates, such as ATP, GTP, UTP, and CTP and without the target amino acids was prepared (Examples 1-1 and 1-2).

In the present invention, the step (b) is a step of performing cell-free protein synthesis by mixing an assay sample containing the target amino acids with the reaction mixture for cell-free protein synthesis, and the step may further include a step of mixing the reaction mixture and the assay sample, and incubating the mixture.

In particular, "target amino acid", "reaction mixture for cell-free protein synthesis" and "cell-free protein synthesis" are as described above.

As used herein, the term "assay sample" refers to a sample which contains the target amino acids and is applied to the method of the present invention.

Specifically, the assay sample may be derived from at least one selected from the group consisting of a feed, food, or chemical substance.

Additionally, the assay sample may be isolated from a living organism, and more specifically, it may be at least one selected from the group consisting of blood, plasma, serum, cancer tissue, and cancer cell, or it may be heat treated and filtered as a pre-treatment, but is not limited thereto.

In a specific embodiment of the present invention, as it was confirmed that the FBS contains a component that interferes with the cell-free protein synthesis reaction, the FBS was heat-treated to solve this problem, and the resulting aggregates were removed by filtration and the filtered FBS was used in the method of the present invention. As a result, it was confirmed that the amino acids contained in FBS could be quantified (Examples 1-4 and FIG. 4).

In particular, the term "living organism" is an organism containing amino acids, and may include, without limitation, mammals, including rats, livestock, humans, etc., farmed fish, etc.

Additionally, for the purpose of the present invention, the assay sample may contain the target amino acids.

Additionally, the assay sample may be isolated from a patient with an amino acid metabolism-related disease, and specifically, the amino acid metabolism-related disease may be an amino acid metabolic disorder or cancer.

As used herein, the term "amino acid metabolic disorder" is a disease that induces a decrease or an increase in specific amino acids in the body. It is known to occur due to lack or reduced activity of an enzyme involved in a specific amino acid metabolism process, and patients suffering from this disease are clearly distinguished from normal people in terms of the concentration of amino acids in the body. Specifically, the amino acid metabolic disorder may be at least one selected from the group consisting of arginase deficiency, cystinuria, maple syrup urine disease, hyperlysinemia, homocystinuria, hypermethioninemia and phenylketonuria, but is not limited thereto.

More specifically, the arginase deficiency may be caused by arginine; the cystinuria may be caused by arginine or lysine; the maple syrup urine disease may be caused by isoleucine or valine; the hyperlysinemia may be caused by lysine; the homocystinuria may be caused by methionine; the hypermethioninemia may be caused by methionine; and the phenylketonuria may be caused by phenylalanine or tyrosine, but is not limited thereto.

Additionally, plasma free amino acids are redistributed or translocated to support the growth and development of cancer, and thus, the concentration (profile) of amino acids in the body of cancer patients is clearly distinguished from those of normal people.

In a specific embodiment of the present invention, the cell-free protein reaction mixture prepared as an assay sample was mixed with pre-treated FBS and after incubation, the cell-free protein synthesis was carried out (Example 1-4). Additionally, it was confirmed that the cell-free protein synthesis could be carried out when assay samples containing amino acids (arginine, isoleucine, leucine, lysine, methionine, phenylalanine, tyrosine, or valine) associated with various amino acid metabolic disorders (Example 1-3) were used.

In the present invention, the step (c) is a step of measuring the signal intensity of the synthesized protein.

In particular, the signal intensity of the protein may be measured by a method known in the art.

Specifically, it may be measured using a measuring device capable of detecting a signal of a protein, and more specifically, it may be measured using a TRIAD multimode detector, Wallac/Victor fluorescence, Perkin-Elmer LB50B luminescence spectrometer, luminometer, spectrophotometer, cyclic voltammetry (CV), etc., but is not limited thereto.

Alternatively, the step (c) may be carried out by a method of producing glucose using the activity of the cell-free synthesized protein and quantifying the produced glucose using a glucose meter. Specifically, it is possible to estimate the activity of invertase by producing the corresponding invertase in a cell-free synthetic solution containing an *E. coli*-derived invertase gene and incubating the invertase by adding it to a solution containing sucrose, and then measuring the produced glucose using a glucose meter. Since the estimated activity of the invertase is proportional to the amino acid concentration in the cell-free synthesis sample, the concentration of amino acids in the sample can be measured by measuring the concentration of glucose. In addition to the above-described invertase, maltase that produces glucose from maltose, glucoamylase that produces glucose from starch, etc., may be used in the amino acid analysis based on such principle, but is not limited thereto.

In the present invention, the step (d) is a step of calculating the concentration of the target amino acids by comparing the intensity of the measured signal with a standard concentration curve for each amino acid according to the signal of the protein prepared using a standard sample.

As used herein, the term "standard sample" includes each amino acid at a specific concentration, and specifically, it may contain each amino acid at a concentration of 0.01 to 100 μM, but is not limited thereto.

When the cell-free protein synthesis is performed using the standard sample, the signal of the protein corresponding to the specific concentration of each amino acid can be determined, and accordingly, the concentration of each amino acid according to the signal of the protein can be determined. Therefore, the standard concentration curve for each amino acid according to the signal of the protein includes information on the signal of the protein according to the specific concentration of the amino acid, and thus the concentration of the target amino acids can be calculated by comparing the signal intensity measured according to the steps (a) to (c) with the concentration curve.

In particular, for the purpose of the present invention, the concentration of the target amino acids is calculated by comparing with the standard concentration curve produced using the target amino acids as a standard sample.

In the present invention, the method for quantification of amino acids according to the present invention can quantify the amino acids at concentrations of 10 nM to 150 µM, specifically, 50 nM to 130 µM, more specifically, 100 nM to 110 µM, even more specifically, 130 nM to 100 µM, but is not limited thereto.

In a specific embodiment of the present invention, reaction mixtures of cell-free protein synthesis containing components necessary for the synthesis of cell-free proteins such as E. coli strain BL21-Star (DE3) cell extract, plasmids containing polynucleotides encoding sfGFP, and ribonucleoside triphosphates such as ATP, GTP, UTP, and CTP and without the target amino acids were prepared (Examples 1-1 and 1-2). The cell-free protein reaction mixtures were mixed with the standard sample only containing the target amino acids (arginine, isoleucine, leucine, lysine, methionine, phenylalanine, tyrosine, or valine) and incubated to carry out the cell-free protein synthesis, thereby producing the standard concentration curve for each amino acid according to the sfGFP fluorescent signal (Example 1-3 and FIG. 3). Thereafter, in order to quantify the target amino acids contained in the fetal bovine serum (FBS), an assay sample, the FBS was heat-treated and filtered (Example 1-4) and mixed with the reaction mixtures. After incubation, the cell-free protein synthesis was carried out. Then, the target amino acids such as alanine, cysteine, serine, glycine, histidine, threonine, proline or tryptophan were quantified by comparing the detected sfGFP fluorescence intensity with the standard concentration curve, and their concentrations were found to be in the range of about 130 nM to 100 µM (FIGS. 7 and 8).

These results show that the cell-free protein synthesis system can be successfully employed by the method for quantification of amino acids according to the present invention, suggesting that amino acids can be quantified in a short time at a low cost.

Another aspect of the present invention provides a method of providing information for diagnosing an amino acid metabolism-related disease, including comparing the concentration of amino acids quantified according to the method for quantification of amino acids with a normal control group.

Additionally, the method may be a method for diagnosing an amino acid metabolism-related disease, specifically, an amino acid metabolic disorder or cancer, and the amino acid metabolic disorder and cancer are as described above.

Since patients with the amino acid metabolism-related disease have a concentration (profile) of amino acids in the body different from those of normal people as a direct or indirect result of the disease, the method for quantification of amino acids according to the present invention can be used to diagnose the disease.

Specifically, the method may be a method for providing information for diagnosing an amino acid metabolism-related disease or a method for diagnosing the same, including (a) performing the method for quantification of amino acids according to the invention using an assay sample isolated from a patient having an amino acid metabolic-related disease; and (b) comparing the concentration of the amino acids quantified in step (a) with a normal control group and judging the patient as having the amino acid metabolism-related disease when the concentration of the amino acids is lower or higher than those of the normal control.

In particular, the assay sample is as described above, and since the specific concentration (profile) of the amino acids exhibited by the disease is known in the art, those skilled in the art may be able to easily distinguish patients with the amino acid metabolism-related disease by the method according to the invention, specifically by the steps (a) and (b).

Still another aspect of the present invention provides a method for screening a substance for prevention or treatment of an amino acid metabolism-related disease, including:

(a) treating a candidate material for prevention or treatment of amino acid metabolism-related disease with an assay sample isolated from a living organism;

(b) measuring the concentration of target amino acids contained in the assay sample treated with the candidate material according to the method; and (c) comparing the amino acid concentration of step (b) with a normal control group.

In particular, the assay sample is as described above, and specifically, it may be isolated from a patient having an amino acid metabolism-related disease.

As used herein, the term "candidate material for prevention and treatment of an amino acid metabolism-related disease" refers to a material that is expected to be able to treat the amino acid metabolism-related disease, and any material that is expected to be able to directly or indirectly alleviate or improve the amino acid metabolism-related disease can be used without limitation, and additionally, it includes all materials expected to show a therapeutic effect such as chemical compounds, genes, or proteins, etc.

In the present invention, the step (a) of treating a candidate material for the prevention or treatment of an amino acid metabolism-related disease with an assay sample may be carried out by a method known in the art. As a specific example, the candidate material may be treated by incubating the candidate material with an assay sample, or by administering the material in vivo, but is not limited thereto. Those skilled in the art will be able to employ a method suitable for the purpose of the present invention.

Additionally, the step (b) of measuring the concentration of target amino acids contained in the assay sample may be carried out by the method according to the present invention.

Lastly, the step (c) is a step of deciding whether the candidate material can be used as a prophylactic or therapeutic material for the amino acid metabolism-related disease. Patients with the amino acid metabolism-related disease have a concentration (profile) of amino acids in the body different from those of normal people, and thus, candidate materials that exhibit the same or similar amino acid concentration as normal control can be used as a prophylactic or therapeutic material for the amino acid metabolism-related disease.

Still another aspect of the present invention provides a method for screening transaminase substrate, including:

(a) reacting a transaminase with a mixture of a candidate amine donor substrate and amine acceptor substrate;

(b) measuring the concentration of amino acids contained in the reaction solution after completion of the reaction; and (c) comparing the amino acid concentration of step (b) with a control group The screening method may be a method of screening candidate materials by confirming the concentration of amino acids produced by the transamination reaction through the quantification of amino acid for cell-free protein synthesis.

As used herein, the term "transaminase" refers to an enzyme that catalyzes the biochemical reaction between amino acids and α-keto acids to remove the amino groups and transfer them to other molecules. Specifically, the enzyme catalyzes the reaction by which the amino group is removed from the amino acid to produce α-keto acid, and then the amino group is transferred to another α-keto acid having no amino group thereby producing a new amino acid.

The amine donor substrate refers to a substrate having an amine group and is capable of delivering an amine group by an enzyme or catalyst. Additionally, the amine acceptor substrate refers to a substrate capable of receiving an amine group by an enzyme or catalyst.

Specifically, the transaminase catalyzes the reaction by which a primary amine group of an amine donor substrate is exchanged with a ketone group of an amine accepting substrate. As a result, the amine group of the donor substrate is substituted with the ketone group, and the ketone group of the acceptor substrate is substituted with the amine group.

Therefore, as the amine donor substrate to be applied in the present invention, various compounds having a primary amine group may be used, and as the amine acceptor substrate, substrates, in which a ketone group is converted to an amino acid by substitution with an amine group, may be used.

For example, in the case of pyruvic acid, alanine is produced as the ketone group is substituted with an amine group, and glutamate is produced when alpha-ketoglutarate is used as the amine acceptor substrate. Additionally, when oxaloacetate is used as the amine acceptor substrate, aspartate is produced, and thus, the activity of the transaminase can be measured by the present invention.

The step of measuring the concentration of the amino acid in the step (b) may be measured by the method for quantification of amino acids according to the cell-free protein synthesis. In a specific embodiment of the present invention, in order to screen various substrates through transaminase, the reaction product produced by reacting the substrate with the enzyme was subjected to the quantification of amino acids according to the cell-free protein synthesis, and it was confirmed that the substrates could be screened through the difference in the amino acid level for each substrate (FIG. 12).

Still another aspect of the present invention provides a method for screening a transaminase, including:

(a) reacting a candidate enzyme with a mixture of an amine donor substrate and amine acceptor substrate;

(b) measuring the concentration of amino acids contained in the reaction solution after the completion of the reaction; and (c) comparing the amino acid concentration of step (b) with a control group.

The transaminase, the amine donor substrate, and the amine acceptor substrate are as described above.

The step of measuring the concentration of the amino acid in the step (b) may be measured by the method for quantification of amino acids according to the cell-free protein synthesis.

As the screening method of the transaminase, a method developed by applying the method for quantification of amino acids according to the cell-free protein synthesis to a conventionally known method for screening transaminase (Mathew, Sam, et al., 2013; Truppo, Matthew D., et al., 2009) was used. Thus, it can be implied that the transaminase having excellent activity can be screened through the screening method.

MODE FOR CARRYING OUT THE INVENTION

Hereinafter, the present invention will be described in more detail by way of Examples. However, these Examples are given for illustrative purposes only, and the scope of the invention is not intended to be limited to or by these Examples Example 1. Construction of Method for Quantification of Amino Acids Using Cell-Free Protein Synthesis System Example 1-1. Method for Obtaining Cell Extract for Cell-Free Protein Synthesis The cell extract used to construct the cell-free protein synthesis system of the present invention was obtained according to a known method (Korean Patent No. 10-0733712).

Specifically, E. coli strain BL21-Star (DE3) cells were incubated in 3 L of 2×YTPG at 37° C. To induce the expression of T7 RNA polymerase, 1 mM isopropyl-thiogalactopyranoside (IPTG) was added to the culture broth when the absorbance ($OD_{600}$) reaches 0.6. The cells were harvested when the absorbance ($OD_{600}$) reached 4.5 and washed tree times with 20 ml of wash buffer [10 mM Tris-acetate buffer (pH 8.2), 14 mM magnesium acetate, 80 mM potassium acetate, 1 mM dithiothreitol (DTT), 0.05% (v/v) 2-mercaptoethanol (2-ME) per gram of wet cells]. The washed cells (10 g) were re-suspended in 12.7 ml of lysis buffer (wash buffer without 2-ME) and lysed using a French Pressure Cell Press (Thermo Scientific, Waltham, Mass.) at a constant pressure (20,000 psi).

Thereafter, the cell lysate was centrifuged twice at 12,000 g for 30 minutes twice to obtain a supernatant (hereinafter, designated as 'S12 extract'). To remove the residual amino acids, the S12 extract was centrifuged in a Vivaspin centrifugal concentrator (Sartorius Stedim Biotech GmbH, Gottingen, Germany) with a 50,000 Da molecular weight cut-off membrane. After addition of 18 mL of wash buffer to 2 mL of S12 extract, the centrifugation process was repeated 3 times at 2,000 g to reduce the volume of the diluted extract to the original volume (2 ml). Lastly, aliquots of the S12 extract was flash frozen and stored at −80° C.

Example 1-2. Amino Acids Analysis Method

In order to construct a method for quantification of amino acids using a cell-free protein synthesis system, the following procedure was performed.

First, reaction mixtures of cell-free protein synthesis (hereinafter, referred to as "reaction mixtures") consisting of 57 mM HEPES-KOH, pH 8.2; 1.2 mM ATP; 0.85 mM each of CTP, GTP, and UTP; 80 mM ammonium acetate; 12 mM magnesium acetate; 80 mM potassium acetate; 34 μg/mL 1,5-formyl-5,6,7,8-tetrahydrofolic acid; 2 mM each of amino acid; 2% polyethylene glycol (PEG) 8000; 3.2 U/ml of creatine kinase; 67 mM creatine phosphate; 24% (v/v)

filtered S12 extract; and 6.7 μg/mL of superfolder green fluorescent protein (sfGFP) plasmid were prepared.

Thereafter, 20 μl of an incomplete reaction mixture without the target amino acid was mixed with 10 μl of assay samples containing the target amino acid to be quantified. After a 1 hour of incubation at 30° C., the cell-free synthesis reactions were carried out. In particular, the incomplete reaction mixture was prepared without the target amino acid to be quantified when preparing the reaction mixtures.

The sfGFP fluorescence intensity signals produced through the cell-free synthesis reaction were measured, and the amino acids were quantified by comparing with a standard curve determination of the amino acid concentration. Additionally, in order to confirm the significance of the analysis results, the intensity signals were compared with the values confirmed through a Hitachi L-8900 amino acid analyzer (Hitachi High-Technologies, Tokyo, Japan).

The SPSS Version 22.0 software (SPSS Inc., Chicago, Ill.) was used for all statistical analyses. $P>0.05$ was considered to be statistically indifferent.

Example 1-3. Confirmation of Amino Acid Concentration According to sfGFP Fluorescence Signals In order to construct a method for quantification of amino acids using a cell-free protein synthesis system, first, a standard concentration curve for each amino acid according to the sfGFP fluorescence signals was prepared using a standard sample containing only the target amino acids at specific concentrations.

Meanwhile, as shown in FIG. 1, the method for quantification of amino acids of the present invention works by complementing the reaction mixture containing 19 amino acids with the missing amino acids in the assay sample. For example, a cell-free synthesis reaction mixture devoid of lysine will only make truncated protein fragments and fail to generate a sfGFP fluorescence signal from the template DNA because ribosomes will stall at lysine codons of mRNA. Upon the addition of an assay sample containing lysine, however, translation can proceed to completion to produce full-length sfGFP and consequently, a fluorescence signal is produced. Accordingly, the present inventors have focused on the finding that the intensity of the sfGFP fluorescence signal is proportional to the amino acid titer contained in the assay sample, and thus developed the method for quantification of amino acids of the present invention.

Specifically, eight amino acids such as arginine, isoleucine, leucine, lysine, methionine, phenylalanine, tyrosine, and valine, which are associated with different amino acid metabolic disorders, as shown in Table 1, were selected, as target amino acids.

TABLE 1

| Amino Acids | Related Disease |
|---|---|
| Arginine | Arginase deficiency and Cystinuria |
| Isoleucine | Maple syrup urine disease |
| Leucine | |
| Lysine | Hyperlysinemia |
| Methionine | Homocystinuria, Hypermethioninemia |
| Phenylalanine | Phenylketonuria |
| Tyrosine | |
| Valine | Maple syrup urine disease |

Then, a linear standard curve of amino acid concentration according to the sfGFP fluorescence intensity was prepared using the standard sample containing various concentrations of the amino acids.

As a result, as shown in FIG. 2, it was confirmed that the standard curve showed a linear curve even when the concentration of the amino acid was relatively high, about 100 μM, and the sfGFP fluorescence was detected even when the concentration of the amino acid was low, about 130 nM to 980 nM.

From the above results, it was confirmed that the method of the present invention can be utilized for quantification of the eight amino acids, and a wide range of amino acid concentration from 130 nM to 100 μM could be possible for quantification.

Example 1-4. Establishment of Method for Quantification of Amino Acids Using Biological Assay Samples In order to confirm whether the amino acids contained in a biological sample can be quantified by the method of the present invention, fetal bovine serum (FBS) was used as an assay sample.

Specifically, 5 μl of FBS was diluted 4-fold in water and added to incomplete reaction mixtures. After a 1 hour of incubation, 15 μl of the mixture was withdrawn and diluted in 200 μl of phosphate buffered saline (PBS), and the fluorescence intensity was measured.

As a result, as shown in FIG. 3A, the cell-free protein synthesis reactions were not activated by the addition of FBS, and sfGFP was not produced. As no sfGFP fluorescence signals were produced, the sfGFP fluorescence signal from all eight cell-free synthesis reactions was only comparable to that from a negative control reaction conducted in the absence of sfGFP DNA.

However, as shown in FIG. 3B, as a result of analyzing the amino acids contained in the FBS using a standard amino acid analyzer, it was confirmed that the FBS contained the eight target amino acids at concentrations of 35 μM to 420 μM, and that their concentrations were within or exceeded the range for the standard curves prepared in Example 2.

From the results above, it was found that the FBS contained certain component that interferes with the cell-free protein synthesis reactions of the present invention.

Accordingly, in order to reduce the inhibitory effect of the cell-free protein synthesis reaction in FBS, FBS was subjected to heat treatment and then used for analysis. Specifically, FBS was heat-treated at 80° C. for 10 minutes, and protein aggregates formed during the heat treatment were removed using a centrifuge.

As a result, as shown in FIG. 4A, when the unheat-treated FBS was used as an assay sample, the cell-free protein synthesis reaction was inhibited and the sfGFP fluorescence signals rapidly decreased, but when the heat-treated and filtered FBS was used as an assay sample, the sfGFP fluorescence signals were maintained at a high level.

Additionally, as shown in FIG. 4B, it was confirmed that 23S rRNA, 16S rRNA and mRNA were degraded when the unheat-treated FBS was used.

In contrast, as can be seen in FIG. 4 C, the degradation of RNA species was not observed when the heat-treated and filtered FBS was used.

From the above results, it appeared that there existed components that inhibited the cell-free protein synthesis reaction in FBS, and these have nuclease activity that degrades RNA, etc. However, it was observed that the inhibitory effect thereof was removed when the FBS was heat treated and filtered.

Accordingly, it was found that it is preferred to use the assay sample which is heat treated and from which aggregates formed are removed in the method of the present invention.

Example 1-5. Method for Quantification of Amino Acids in Biological Samples Using Glucose Meter Cell-free protein synthesis reaction was performed under the same conditions as described in Example 1-2. However, invertase was produced through the cell-free synthesis reaction using the invertase gene rather than the sfGFP gene as a template nucleotide of the cell-free synthesis reaction. After the cell-free synthesis, 10 μL of the reaction solution was mixed with the same volume of sucrose solution (100 mM potassium acetate, 100 mM sucrose, pH 6.0) and reacted at 25° C. for 5 minutes. After completion of the glucose production reaction by heating at 95° C. for 5 minutes, 5 μL of the supernatant was collected and the amount of glucose produced was measured using a glucose meter (Accu-check, Roche Diagnostics) (FIG. 5).

Example 2. Confirmation of Significance of Method for Quantification of Amino Acids Using Cell-Free Protein Synthesis System Example 2-1. Confirmation of Significance of Method for Quantification of Amino Acids in Biological Samples by Measuring Fluorescent Protein Produced in Cell-Free Protein Synthesis System In order to confirm the significance of the method for quantification of amino acids developed according to Example 1-2, the amino acids contained in the assay sample were quantified using the heat treated and filtered FBS as an assay sample.

As a result, as shown in FIG. 6A, it was confirmed that all eight incomplete reaction mixtures devoid of arginine, isoleucine, leucine, lysine, methionine, phenylalanine, tyrosine or valine generated the sfGFP fluorescence signals.

Additionally, as shown in FIG. 6B, the concentration of each amino acid was determined by substituting the sfGFP fluorescence signals into the standard curve, and as a result, it was confirmed that the concentrations of amino acids quantified by the present method were very similar to those confirmed through the standard HPLC analysis.

Further, as can be seen in FIGS. 7 and 8, it was confirmed that the most amino acids contained in the FBS could be quantified by the method of the present invention, and specifically, alanine, cysteine, serine, glycine, histidine, threonine, proline or tryptophan could also be quantified, in addition to the eight amino acids.

Example 2-2. Confirmation of Significance of Method for Quantification of Amino Acids in Biological Samples Using Glucose Meter In order to confirm the significance of the method for quantification of amino acids developed according to Example 1-5, the amino acids contained in the assay sample were quantified using the heat treated and filtered FBS as an assay sample.

As a result, as shown in FIGS. 9 and 10, it can be found that all eight incomplete reaction mixtures devoid of arginine, isoleucine, leucine, lysine, methionine, phenylalanine, tyrosine or valine could be measured by the glucose meter. As a result of confirming the concentration of each amino acid by substituting the values measured by the glucose meter into the standard curve, it was confirmed that the concentrations of the amino acids quantified by the method of the present invention were very similar to those confirmed by the standard HPLC analysis.

Example 3. Confirmation of Significance of Method for Quantification of Amino Acids Using Mixture of Recombinant Proteins In order to develop a more efficient method for quantification of amino acids, recombinant proteins prepared using recombinant techniques were used for cell-free protein synthesis, instead of cell extracts.

Specifically, cell extracts contain enzymes that use amino acids as substrates, which may cause a problem that the target amino acids may not be quantified. Thus, the components necessary for cell-free protein synthesis were each prepared by recombinant techniques known in the art in order to exclude the above-mentioned enzymes from the recombinant protein reaction mixtures, and these components were mixed, and the cell-free protein synthesis according to Examples 1-2 above was carried out. In particular, initiation factors, elongation factors, release factors, termination factors, aminoacyl-tRNA synthetases, methionyl-tRNA transformylase, RNA polymerase, ribosomes, etc. were prepared and used.

As a result, as shown in FIG. 11, it was confirmed that the amino acids could be quantified by the cell-free protein synthesis using recombinant proteins, instead of cell extracts, and specifically, it was confirmed that aspartic acid, asparagine, glutamic acid, or glutamine could also be quantified.

Example 4. Screening of Transaminase Substrates by Cell-Free Protein Synthesis

The screening effect was confirmed by applying the cell-free protein synthesis method and the method for quantification of amino acids to the screening of the transaminase substrate.

Transaminase (in this example, a transaminase derived from *Vibrio fluvialis*), an amine donor substrate to be screened (one selected from S01, α-methylbenzylamine; S02, benzylamine; S03, 3-phenyl-1-propylamine; S04, phenylbutyl amine; S05, propylamine; S06, amylamine; S07, isopropylamine; S08, sec-butylamine; S09, β-alanine; S10, phenylalanine), and an amine acceptor substrate (in this example, pyruvic acid was used) were used. Specifically, 50 mM Tris-HCl (pH 7.2), 10 mM amine donor substrate, 10 mM amine acceptor substrate, 20 μM pyridoxal-5'-phosphate, and 10 μl transaminase were reacted at 37° C. and 1000 rpm for 3 hours The reaction solution obtained in the above process was diluted with an appropriate dilution factor and added to a cell-free protein synthesis reaction solution devoid of alanine, which is the reaction product of the transamination reaction of pyruvic acid. The reaction mixtures consisting of 57 mM HEPES-KOH (pH 7.5); 1.2 mM ATP; 0.85 mM each of CTP, GTP, and UTP; 2 mM DTT; 90 mM potassium glutamate; 80 mM ammonium acetate; 12 mM magnesium acetate; 67 μg/mL 1,5-formly-5,6,7,8-tetrahydrofolic acid; 2 mM each of 19 amino acids except alanine; 2% PEG 8000; 67 mM CP; 3.2 µg/mL CK; 13 µg/mL template DNA; 40 µl of S12 extract; and 3 µl of transaminase were prepared in a final volume of 150 µl at 30° C. for 3 hours to measure the sfGFP expression. The amount of alanine produced from pyruvic acid in the transamination reaction was determined by comparing the measured fluorescence values with the standard curve measured for each alanine concentration.

As a result, as shown in FIG. 12, it was confirmed that the alanine concentration varied depending on the substrate, thereby confirming that the transaminase substrate could be screened using the method.

Those of ordinary skill in the art will recognize that the present invention may be embodied in other specific forms without departing from its spirit or essential characteristics. The described embodiments are to be considered in all respects only as illustrative and not restrictive. The scope of the present invention is therefore indicated by the appended claims rather than by the foregoing description. All changes which come within the meaning and range of equivalency of the claims are to be embraced within the scope of the present invention.

The invention claimed is:

1. A method for quantification of a target amino acid, comprising:
   (a) preparing a reaction mixture for cell-free protein synthesis of a reporter protein comprising the target amino acid, wherein the reaction mixture comprises a mixture of amino acids for synthesizing the reporter protein which mixture does not include the target amino acid;
   (b) performing cell-free protein synthesis by mixing an assay sample containing the target amino acid with the reaction mixture for cell-free protein synthesis;
   (c) measuring the signal intensity of the synthesized reporter protein; and
   (d) calculating the concentration of the target amino acid by comparing the measured signal intensity with a standard curve of the signal intensity of the reporter protein as a function of the concentration of the target amino acid in a standard sample.

2. The method of claim 1, wherein the reaction mixture for the cell-free protein synthesis comprises a cell extract or a mixture of recombinant proteins.

3. The method of claim 2, wherein the cell extract is an extract of *E. coli*, wheat germ, rabbit reticulocytes, yeast, Chinese Hamster Ovary cells, or HeLa cells.

4. The method of claim 2, wherein the recombinant protein is at least one selected from the group consisting of an initiation factor, elongation factor, release factor, termination factor, aminoacyl-tRNA synthetases, methionyl-tRNA transformylase, RNA polymerase, and ribosome.

5. The method of claim 1, wherein the reaction mixture for the cell-free protein synthesis comprises a polynucleotide encoding a reporter protein.

6. The method of claim 5, wherein the reporter protein is a super-folder green fluorescent protein (sfGFP), green fluorescent protein (GFP), yellow fluorescent protein (YFP), red fluorescent protein (RFP), mCherry fluorescent protein, lactamase, galactosidase, horseradish peroxidase (HRP), or glucose oxidase.

7. The method of claim 1, wherein the assay sample is derived from at least one selected from the group consisting of a feed, food or chemical substance.

8. The method of claim 1, wherein the assay sample is isolated from a living organism.

9. The method of claim 8, wherein the assay sample is at least one selected from the group consisting of blood, plasma, serum, cancer tissue, and cancer cell.

10. The method of claim 8, wherein the assay sample is heat treated and filtered.

11. The method of claim 8, wherein the assay sample is isolated from a patient with an amino acid metabolism-related disease.

12. The method of claim 11, wherein the amino acid metabolism-related disease is an amino acid metabolic disorder or cancer.

13. The method of claim 12, wherein the amino acid metabolic disorder is at least one selected from the group consisting of arginase deficiency, cystinuria, maple syrup urine disease, hyperlysinemia, homocystinuria, hypermethioninemia, and phenylketonuria.

14. The method of claim 1, wherein the method is used to quantify the target amino acid at a concentration of 10 nM to 150 uM.

15. A method for screening a substance for prevention or treatment of an amino acid metabolism-related disease, comprising:
   (a) treating a candidate material for prevention or treatment of an amino acid metabolism-related disease with an assay sample isolated from a living organism;
   (b) measuring the concentration of a target amino acid contained in the assay sample treated with the candidate material according to the method of claim 1; and
   (c) comparing the amino acid concentration of step (b) with a normal control group.

16. The method of claim 15, wherein the amino acid metabolism-related disease is an amino acid metabolic disorder or cancer.

17. The method of claim 16, wherein the amino acid metabolic disorder is at least one selected from the group consisting of arginase deficiency, cystinuria, maple syrup urine disease, hyperlysinemia, homocystinuria, hypermethioninemia, and phenylketonuria.

18. A method for screening a transaminase substrate, comprising:
   (a) reacting a transaminase with a mixture of a candidate amine donor substrate and amine acceptor substrate;
   (b) measuring the concentration of a target amino acid contained in the reaction solution after completion of the reaction, wherein the measuring of the amino acid concentration is performed by the method of claim 1; and
   (c) comparing the amino acid concentration of step (b) with a control group.

19. A method for screening a transaminase, comprising:
   (a) reacting a candidate enzyme with a mixture of an amine donor substrate and amine acceptor substrate;
   (b) measuring the concentration of a target amino acid contained in the reaction solution after completion of the reaction, wherein the measuring of the amino acid concentration is performed by the method of claim 1; and
   (c) comparing the amino acid concentration of step (b) with a control group.

* * * * *